US010185806B1

(12) United States Patent
Piacentile

(10) Patent No.: US 10,185,806 B1
(45) Date of Patent: Jan. 22, 2019

(54) SYSTEMS AND METHODS FOR WIRELESS PRESCRIPTION ADVERTISING

(71) Applicant: LB Financial Holdings, LLC, Minden, NV (US)

(72) Inventor: Joseph Piacentile, Woodcliff Lake, NJ (US)

(*) Notice: Subject to any disclaimer, the term of this patent is extended or adjusted under 35 U.S.C. 154(b) by 0 days.

(21) Appl. No.: 14/247,174

(22) Filed: Apr. 7, 2014

Related U.S. Application Data

(63) Continuation of application No. 10/951,212, filed on Sep. 27, 2004, now Pat. No. 8,694,329.

(Continued)

(51) Int. Cl.
*G16H 20/00* (2018.01)
*G06F 19/00* (2018.01)

(52) U.S. Cl.
CPC .......... *G06F 19/326* (2013.01); *G06F 19/328* (2013.01); *G06F 19/3456* (2013.01); *G16H 20/00* (2018.01)

(58) Field of Classification Search
CPC ............ G06Q 50/22; G06Q 50/24; G06F 19/322–19/327; G06F 19/30; G06F 19/34; G06F 19/3456; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00;

(Continued)

(56) References Cited

U.S. PATENT DOCUMENTS

| 4,774,655 | A | 9/1988 | Kollin et al. |
| 5,016,172 | A | 5/1991 | Dessertine |

(Continued)

OTHER PUBLICATIONS

"U.S. Appl. No. 10/951,212, Advisory Action dated Nov. 8, 2010", 2 pgs.

(Continued)

*Primary Examiner* — Joseph D Burgess
(74) *Attorney, Agent, or Firm* — FisherBroyles, LLP; Ariel Reinitz

(57) ABSTRACT

A medical information system informs prescribers of medically related drug information when preparing a prescription. The point of prescribing messaging system can assist physicians in selecting alternative medications when prescribing medication for patients. The system may include a point of prescription application configured to access and display messages concerning alternative suggested medications of different sponsors in response to an associated selected medication to inform prescribers of the alternative suggested medication for presenting the prescriber with the option of generating an electronic prescription with the alternative suggested medication. A data structure maintained by the system containing associations between a selected trigger medication and a target alternative suggested medication may optionally include additional conditions that control the display of messages such as the gender, age, and/or diagnosis of the patient, the date of the prescription, and/or the region in which the prescription is being made.

21 Claims, 23 Drawing Sheets

Related U.S. Application Data

(60) Provisional application No. 60/506,698, filed on Sep. 26, 2003.

(58) Field of Classification Search
CPC ........ G16H 70/00; G16H 70/20; G16H 70/40; G16H 70/60; G16H 80/00
See application file for complete search history.

(56) References Cited

U.S. PATENT DOCUMENTS

| | | | |
|---|---|---|---|
| 5,408,443 | A | 4/1995 | Weinberger |
| 5,722,418 | A | 3/1998 | Bro |
| 5,737,539 | A * | 4/1998 | Edelson et al. .................... 705/3 |
| 5,845,255 | A * | 12/1998 | Mayaud .............. G06F 19/3456 705/3 |
| 5,995,939 | A | 11/1999 | Berman et al. |
| 6,347,329 | B1 | 2/2002 | Evans |
| 6,421,675 | B1 | 7/2002 | Ryan et al. |
| 6,482,156 | B2 | 11/2002 | Iliff |
| 6,564,121 | B1 | 5/2003 | Wallace et al. |
| 6,656,122 | B2 | 12/2003 | Davidson et al. |
| 6,684,188 | B1 | 1/2004 | Mitchell et al. |
| 6,694,334 | B2 | 2/2004 | Dulong et al. |
| 6,717,598 | B1 | 4/2004 | Melton, Jr. et al. |
| 6,735,497 | B2 | 5/2004 | Wallace et al. |
| 8,694,329 | B1 | 4/2014 | Piacentile |
| 2002/0032583 | A1* | 3/2002 | Joao ................................. 705/2 |
| 2002/0042725 | A1 | 4/2002 | Mayaud |
| 2002/0042726 | A1 | 4/2002 | Mayaud |
| 2002/0165736 | A1 | 11/2002 | Tolle et al. |
| 2003/0036683 | A1 | 2/2003 | Kehr et al. |
| 2003/0050802 | A1 | 3/2003 | Jay et al. |
| 2003/0167190 | A1 | 9/2003 | Rincavage et al. |
| 2004/0002872 | A1 | 1/2004 | Wright |
| 2004/0172295 | A1 | 9/2004 | Dahlin et al. |
| 2004/0267566 | A1 | 12/2004 | Badgett et al. |
| 2006/0265245 | A1 | 11/2006 | Mccallie et al. |

OTHER PUBLICATIONS

"U.S. Appl. No. 10/951,212, Final Office Action dated Mar. 2, 2010", 43 pgs.
"U.S. Appl. No. 10/951,212, Final Office Action dated Oct. 6, 2011", 38 pgs.
"U.S. Appl. No. 10/951,212, Non Final Office Action dated Apr. 15, 2009", 52 pgs.
"U.S. Appl. No. 10/951,212, Non Final Office Action dated May 15, 2013", 36 pgs.
"U.S. Appl. No. 10/951,212, Non Final Office Action dated Dec. 22, 2010", 43 pgs.
"U.S. Appl. No. 10/951,212, Notice of Allowance dated Feb. 7, 2014", 17 pgs.
"U.S. Appl. No. 10/951,212, Notice of Allowance dated Feb. 27, 2014", 14 pgs.
"U.S. Appl. No. 10/951,212, Response filed Jun. 21, 2011 to Non Final Office Action dated Dec. 22, 2010", 33 pgs.
"U.S. Appl. No. 10/951,212, Response filed Oct. 11, 2010 to Final Office Action dated Mar. 2, 2010", 21 pgs.
"U.S. Appl. No. 10/951,212, Response filed Oct. 15, 2009 to Non Final Office Action dated Apr. 15, 2009", 20 pgs.
"U.S. Appl. No. 10/951,212, Response filed Oct. 15, 2013 to Non Final Office Action dated May 15, 2013", 13 pgs.
"U.S. Appl. No. 10/951,212, Response filed Nov. 2, 2012 to Final Office Action dated Oct. 6, 2011", 17 pgs.
"U.S. Appl. No. 11/065,735, Advisory Action dated Oct. 10, 2013", 3 pgs.
"U.S. Appl. No. 11/065,735, Advisory Action dated Nov. 9, 2010", 3 pgs.
"U.S. Appl. No. 11/065,735, Examiner Interview Summary dated May 16, 2013", 3 pgs.
"U.S. Appl. No. 11/065,735, Examiner Interview Summary dated Dec. 11, 2012", 3 pgs.
"U.S. Appl. No. 11/065,735, Examiner Interview Summary dated Dec. 27, 2013", 3 pgs.
"U.S. Appl. No. 11/065,735, Final Office Action dated Feb. 16, 2016", 18 pgs.
"U.S. Appl. No. 11/065,735, Final Office Action dated Mar. 15, 2013", 20 pgs.
"U.S. Appl. No. 11/065,735, Final Office Action dated Oct. 24, 2011", 20 pgs.
"U.S. Appl. No. 11/065,735, Final Office Action dated Nov. 12, 2009", 16 pgs.
"U.S. Appl. No. 11/065,735, Non Final Office Action dated Jan. 5, 2011", 17 pgs.
"U.S. Appl. No. 11/065,735, Non Final Office Action dated Jan. 9, 2009", 14 pgs.
"U.S. Appl. No. 11/065,735, Non Final Office Action dated Oct. 5, 2016", 17 pgs.
"U.S. Appl. No. 11/065,735, Non Final Office Action dated Dec. 30, 2014", 18 pgs.
"U.S. Appl. No. 11/065,735, Response filed Apr. 5, 2017 to Non Final Office Action dated Occt. 5, 2016", 25 pgs.
"U.S. Appl. No. 11/065,735, Response filed Jun. 30, 2015 to Non Final Office Action dated Dec. 30, 2014", 11 pgs.
"U.S. Appl. No. 11/065,735, Response filed Jul. 1, 2011 to Non Final Office Action dated Jan. 5, 2011", 26 pgs.
"U.S. Appl. No. 11/065,735, Response filed Jul. 9, 2009 to Non Final Office Action dated Jan. 9, 2009", 15 pgs.
"U.S. Appl. No. 11/065,735, Response filed Aug. 16, 2016 to Final Office Action dated Feb. 16, 2016", 22 pgs.
"U.S. Appl. No. 11/065,735, Response filed Sep. 15, 2013 to Final Office Action dated Mar. 15, 2013", 10 pgs.
"U.S. Appl. No. 11/065,735, Response filed Oct. 11, 2010 to Final Office Action dated Nov. 12, 2009", 13 pgs.
"U.S. Appl. No. 11/065,735, Response filed Nov. 19, 2012 to Final Office Action dated Oct. 24, 2011", 7 pgs.
"U.S. Appl. No. 11/067,150, Advisory Action dated Sep. 8, 2015", 3 pgs.
"U.S. Appl. No. 11/067,150, Advisory Action dated Nov. 3, 2010", 3 pgs.
"U.S. Appl. No. 11/067,150, Examiner Interview Summary dated Dec. 2, 2013", 3 pgs.
"U.S. Appl. No. 11/067,150, Final Office Action dated Jan. 20, 2010", 20 pgs.
"U.S. Appl. No. 11/067,150, Final Office Action dated May 23, 2013", 17 pgs.
"U.S. Appl. No. 11/067,150, Final Office Action dated Jun. 22, 2015", 24 pgs.
"U.S. Appl. No. 11/067,150, Final Office Action dated Nov. 17, 2016", 27 pgs.
"U.S. Appl. No. 11/067,150, Non Final Office Action dated Apr. 26, 2016", 27 pgs.
"U.S. Appl. No. 11/067,150, Non Final Office Action dated May 29, 2009", 14 pgs.
"U.S. Appl. No. 11/067,150, Non Final Office Action dated Jun. 12, 2017", 33 pgs.
"U.S. Appl. No. 11/067,150, Non Final Office Action dated Aug. 2, 2012", 15 pgs.
"U.S. Appl. No. 11/067,150, Non Final Office Action dated Sep. 9, 2014", 22 pgs.
"U.S. Appl. No. 11/067,150, Non Final Office Action dated Nov. 18, 2013", 16 pgs.
"U.S. Appl. No. 11/067,150, Respone filed Oct. 26, 2016 to Non-Final Office Action dated Apr. 26, 2016", 28 pgs.
"U.S. Appl. No. 11/067,150, Response filed Feb. 4, 2013 to Non Final Office Action dated Aug. 2, 2012", 13 pgs.
"U.S. Appl. No. 11/067,150, Response filed Mar. 9, 2015 to Non Final Office Action dated Sep. 9, 2014", 21 pgs.
"U.S. Appl. No. 11/067,150, Response filed Apr. 6, 2017 to Final Office Action dated Jun. 22, 2015", 20 pgs.
"U.S. Appl. No. 11/067,150, Response filed May 17, 2017 to Final Office Action dated Nov. 17, 2016", 30 pgs.

(56) References Cited

OTHER PUBLICATIONS

"U.S. Appl. No. 11/067,150, Response filed May 19, 2014 to Non Final Office Action dated Nov. 18, 2013", 16 pgs.
"U.S. Appl. No. 11/067,150, Response filed Aug. 24, 2015 to Final Office Action dated Jun. 22, 2015", 20 pgs.
"U.S. Appl. No. 11/067,150, Response filed Oct. 19, 2010 to Final Office Action dated Jan. 20, 2010", 15 pgs.
"U.S. Appl. No. 11/067,150, Response filed Oct. 23, 2013 to Final Office Action dated May 23, 2013", 10 pgs.
"U.S. Appl. No. 11/067,150, Response filed Oct. 29, 2009 to Non Final Office Action dated May 29, 2009", 13 pgs.

\* cited by examiner

| Trigger Medication | Target Alternative | Message | Sponsor | Conditions |
|---|---|---|---|---|
| Medication-A | Medication-B | Message-1 | B | |
| Medication-A | Medication-BB | Message-1 | B | |
| Medication-A | Medication-BBB | Message-2 | B | |
| Medication-A | Medication-C | Message-3 | C | |
| Medication-A | Medication-CC | Message-3 | C | |
| Medication-A | Medication-AA | Message-4 | A | |
| Medication-C | Medication-A | Message-4 | A | |
| Medication-C | Medication-AA | Message-4 | A | |
| Medication-C | Medication-BB | Message-1 | B | |

FIG. 23

| | | | | Condition 1 | Condition 2 | Condition 3 | Condition 4 |
|---|---|---|---|---|---|---|---|
| Trigger Medication | Target Alternative | Message | Sponsor | Age | Gender | Region | Date |
| Medication-A | Medication-B | Message-1 | B | 18 and over | M or F | All | Any |
| Medication-A | Medication-BB | Message-1 | B | under 18 | M or F | Southern | after 1/1/2001 |
| Medication-A | Medication-BBB | Message-2 | B | 2 and over | M or F | Northern | before 1/1/2001 |
| Medication-A | Medication-C | Message-3 | C | 2 to 40 | M | Western | 2/2001 to 2/2004 |
| Medication-A | Medication-CC | Message-3 | C | 2 and over | F | W. and S. | Any |
| Medication-A | Medication-AA | Message-4 | A | 18 and over | M or F | Eastern | Any |
| Medication-C | Medication-A | Message-4 | A | 2 and over | M or F | All | Any |
| Medication-C | Medication-AA | Message-4 | A | 18 and over | M or F | Eastern | Any |
| Medication-C | Medication-BB | Message-1 | B | under 18 | M or F | Southern | after 1/1/2001 |

FIG. 24

SYSTEMS AND METHODS FOR WIRELESS PRESCRIPTION ADVERTISING

CROSS REFERENCE TO RELATED APPLICATIONS

This application is a continuation of U.S. patent application Ser. No. 10/951,212, filed Sep. 27, 2004, which claims the benefit of the filing date of U.S. Provisional Patent Application No. 60/506,698 filed Sep. 26, 2003, the disclosure of each of which is hereby incorporated herein by reference in its respective entirety.

BACKGROUND OF THE INVENTION

The method by which a patient fills a prescription written by his or her doctor has become increasingly complex in the modern health care environment. Most patients with medical insurance must deal with a health care system having four components: an insurer, a physician who is enrolled in the insurer's network, service providers such as pharmacies, hospitals, etc., and the pharmacy benefit manager (PBM)—a management company that manages the pharmacy benefits of the insurer.

The PBM compiles a formulary of medications for the insurer (i.e., a list of medications that the insurer will cover for their enrolled members or that they prefer their members to use for given diagnosis.) In addition, the PBM maintains patient medication histories and other pertinent information related to the safety of the formulary medications for each member. Each PBM is electronically connected to the majority of pharmacies in the nation.

When a prescription is presented at a pharmacy, the pharmacy computer connects to the PBM that manages the pharmacy benefits for that patient. The PBM provides data such as eligibility information, plan details, co-payment requirements and generic options to the inquiring pharmacy. Additionally, the PBM checks to see whether the prescribed medication is within the benefit plan's formulary, and executes a Drug Utilization Review (DUR), which analyzes the prescribed medication versus the patient's known medication and medical history (drug to drug, drug to allergy, drug to medical condition, etc.)

A number of problems can occur during this process if the PBM detects a conflict or potential conflict with the presented script. Formulary variance or contraindication will cause the PMB to signal a notification to the pharmacist. Usually, the pharmacist will make one or more phone calls to the physician to request a change in the prescription in order to make it compliant with the plan, or consistent with the DUR notification. The pharmacist will speak directly to the physician to request any changes being made to the prescription, and any changes are usually entered into the patient's chart. Thus, the current prescription delivery system is increasingly hampered by escalating numbers of necessary phone calls to resolve these prescription-related issues, each of which encroaches on both the pharmacist's and the physician's time.

One attempt to improve the prescription process requires installing custom prescription management software on a local computer within a physician's office, which has the capability of communicating with a remote PBM computer. A physician enters a prescription on a patient's chart, and gives the chart to a staff member (the "user") who enters the prescription information on one or more data entry screens on the local computer. The software directs the local system to connect with the PBM to determine formulary compliance and to perform a DUR. Any problems with the prescription are conveyed to the user, who must then communicate the difficulty to the physician. The physician alters the prescription, and the user repeats the process until an acceptable prescription is found.

Though this approach does reduce the previously required physician-directed phone calls, it still causes considerable disruption. Each time the system indicates a problem, which may occur several times for a single prescription, the user must leave the computer, find and interrupt the physician, and ask that changes be made. It is primarily for this reason that such a system has not been overwhelmingly adopted.

Such systems also do not provide sufficient means for informing prescribers about medications (new or otherwise) that may be appropriately used by their patients for any given problem when prescribing. Traditionally, physicians become aware of potential alternative medications in various ways. Drug sponsors often send sales representatives to meet with prescribers or otherwise send literature to inform them about new medications and treatments. However, such methods tend to inundate prescribers with too much information relating to too many different medications such that the volume of information renders the presentation of information for any individual drug ineffective. Moreover, such information may be presented at inopportune times when the prescriber is not prepared to consider the new drug information or simply is unable to schedule a meeting with a particular representative. It may be desirable to have improvements to these systems for informing prescribers of medicines and alternatives thereto in an electronic prescribing environment while avoiding problems that may result from medication conflicts indicated by a DUR and/or the requirements of a patient or plan specific formulary.

SUMMARY OF THE INVENTION

The invention relates to an automated system for assisting physicians. Generally, the system automatically displays an alternative medication in response to the physician's initiation of a prescription as a way of educating physicians and prescribers about alternative medications at the time of prescribing. In an embodiment, the alternative medication is available for prescribing and is also automatically checked against the patient's record, DUR and formulary before being displayed, such that only a validly prescribable alternative is displayed. Then, the alternative can be prescribed instead of the originally entered medication, and steps taken to complete the fulfillment of the prescription including communication with PBM, entry into patient record, and any necessary communication with a pharmacy (with or without aid of PBM and its network).

Preferably, real-time wireless communication is used to communicate patient specific information and medication specific information to and from remote systems maintaining this information and the physician's prescribing device. Alternatively, the prescribing device can be initialized (synchronized) through wired connector of a cradle at times at beginning of and during the day with patient information, patient's medicines and alternatives for high-speed high volume data transfer and re-synchronized to server with script or prescription information throughout the day, again through a cradle, or alternatively through wireless transmission.

In such a system an embodiment of an invention including a method for prescribing a drug electronically may be implemented. Such a preferred method includes receiving an identifier of a drug to be prescribed to a patient where the identifier identifies a brand name associated with a first entity or a generic name. Then in an automated determining step, the method determines an alternative drug brand name of a second entity based on the identifier by accessing a data structure or querying a database that defines associations between different drug names of different entities and generic names. Then an indication is provided or displayed to a user, that identifies the determined alternative drug brand name. A response may be received from the user indicating whether the alternative drug brand name should be prescribed to the patient. Finally, a prescription is generated for the patient dependent on the response.

In another embodiment, a method of presenting an alternative drug selection to a user of a drug prescription system is provided. The method includes maintaining a table of medications including trigger medications and target medications with each target medication being referenced to at least one of the trigger medications. A user inputs a first drug selection including a trigger medication for a prescription. A device automatically determines from the table at least one of the referenced target medications for presenting in response to the trigger medication. The device automatically presents a message that may suggest the target medication for the prescription. The device then permits the user to prescribe the target medication.

In a preferred embodiment, the message may include information in addition to the suggested drug name and may preferably identify the sponsor (e.g., the maker, seller, retailer or distributor of the suggested drug).

A table or other data structure may be electronically maintained which associates at least some of the trigger medications or target medications to at least one criterion such as region, date, gender, and age. In such a case, data is automatically compared or related to at least one of the user, patient, the location of prescribing and the date of prescribing to the criterion stated in the table. The message that is presented is conditioned on such a comparison or relation.

In an embodiment, a criterion for displaying the message is location, such as whether or not a drug prescription system exists within a particular region. In another embodiment, a message that is displayed according to a trigger medication selection is defined by a sponsor that is associated with or is the same as the sponsor of the trigger medication.

In another embodiment, the method may further include the step of permitting the user to select one or more presented dose and usage instruction(s) for inclusion in an electronic prescription as recommended or contained by the message. Optionally, one such dose and usage instruction message may be a default recommendation of the drug prescription system for incorporation into an electronic prescription based on the prescriber's selection of the suggested alternative medication.

In a particular embodiment, the method permits modifying the first drug selection by deleting the first drug selection, selecting one or more second target medications not equivalent to the first drug selection, and selecting a target medication that is equivalent to the first drug selection.

Additional aspects of the invention will be apparent from a review of the drawings, the following disclosure, and the claims.

BRIEF DESCRIPTION OF THE DRAWINGS

FIG. 23 is an illustrated table data structure assessable to the point of prescription application with associated selected or trigger medications and target or alternative suggested medications of different brands or generic names of various different sponsors (e.g., A, B and C); and FIG. 24 is another example table data structure assessable by the point of prescription application with associations between trigger and target medications also illustrating additional conditions for displaying messages concerning the target medications.

DETAILED DESCRIPTION

Figure 1:
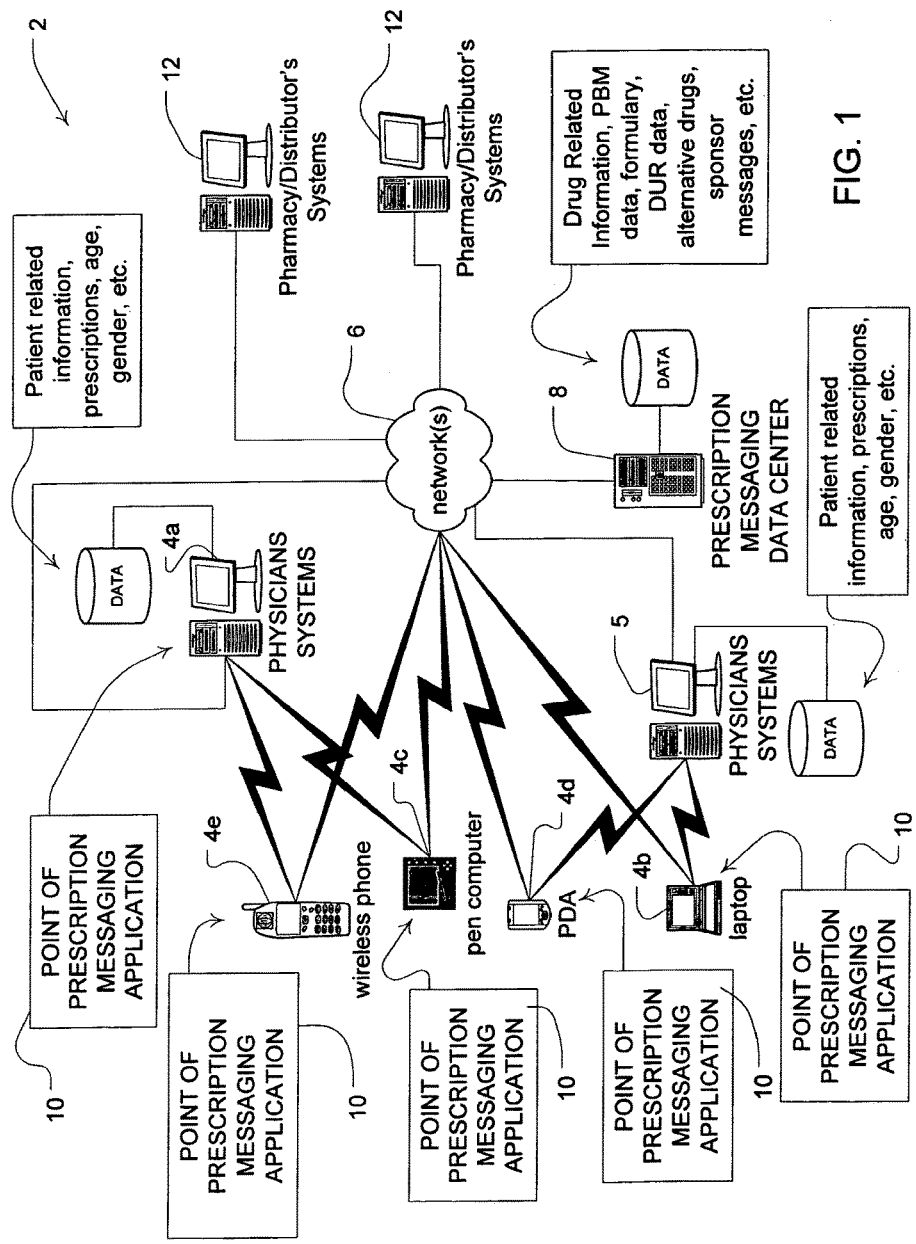
FIG. 1 is a network diagram of an example embodiment including preferred components of a physician assist system of the invention including a point of prescription application.

Referring to the figures, where like numerals indicate similar features, a physician assist system 2 for electronic prescribing of the invention typically includes a prescribing device(s) 4, preferably accessible to a physician, such as a desktop 4a, laptop 4b, hand held or palm computer 4c, a personal data assistant (PDA) 4d or other programmable input/output processing device such as a smart mobile phone 4e. The physician assessable prescribing device 4 may optionally be configured for connection or networking to other systems or computers via one or more communications mechanisms. While such communication links may in part be implemented as a physical connection such as a telephone line, cable or contact based (e.g., cradle) hook-up, in a preferred embodiment, the prescribing device 4 at least includes a communications mechanism that can link the device to other systems via a wireless communications channel. For example, the device may be configured for Bluetooth networking and/or communications over a cellular telephone network for transmitting data or voice. Where such networked communications involve transfer of signals or messages over one or more network(s) 6 that includes an open-type network, such as an internet or the Internet, preferably such signals or messages are encrypted. The network(s) 6 may also include a telephone network, for example, in the event that facsimile transmissions are utilized in the transmission of prescription related messages as discussed in more detail herein.

Figure 2:
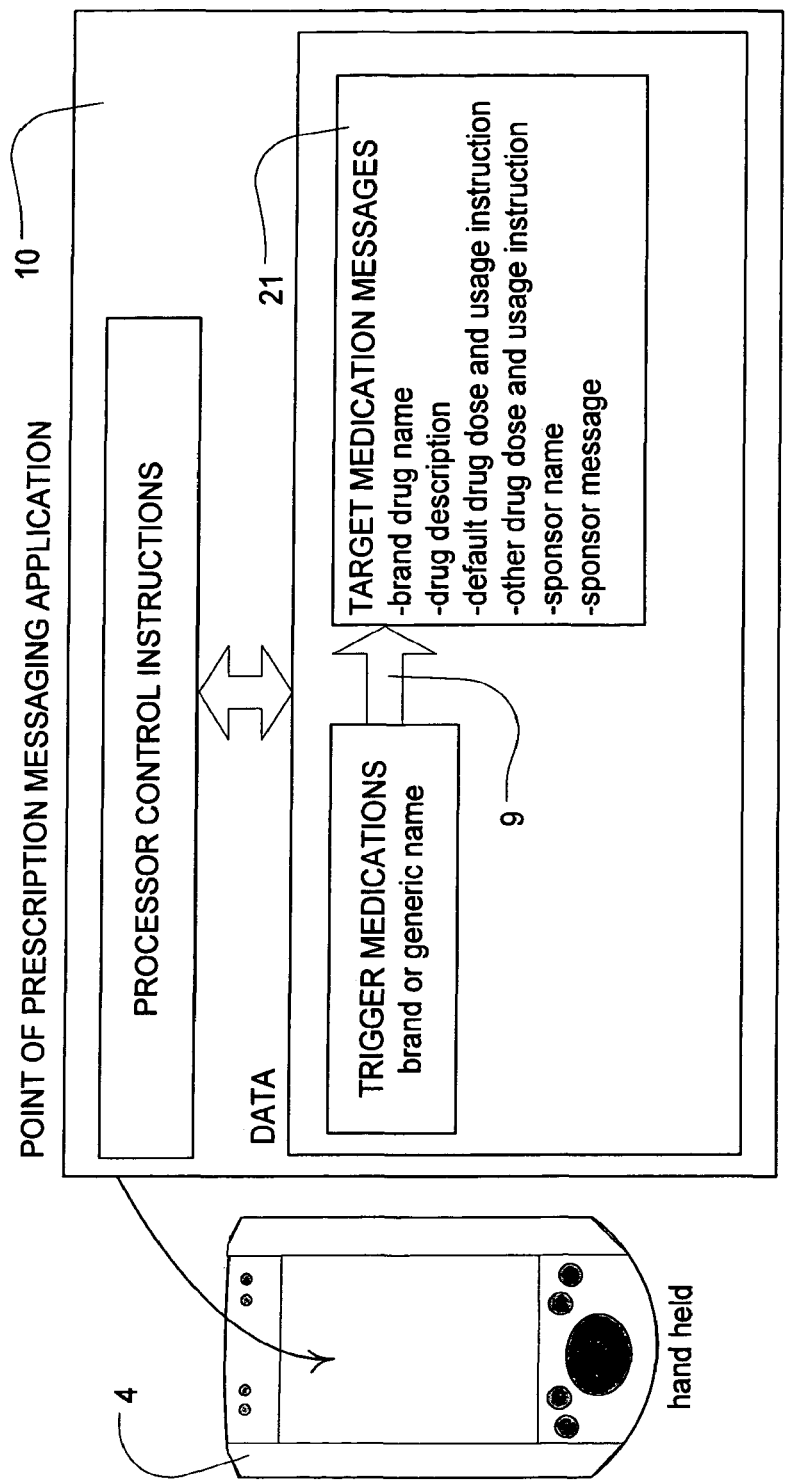
FIG. 2 is an representation of a preferred point of prescription messaging application in a prescribing device with data associations between trigger medications and sponsor messages.

As illustrated in FIG. 2, the physician accessible prescribing device 4 generally includes a processor and memory with processor control instructions and/or other application specific electronic control circuitry. Preferably, such components are for implementing functionality of a point of prescription messaging application 10 of the physician assist system 2. As will be explained in more detailed herein, generally, such application will access or control displaying of medication messages 21 based on medication associations 9 which relate the messages to a medication selected for prescription.

The physician assist system 2 may also include a prescription messaging data center server 8. The data center server 8 is also preferably equipped with one or more communications devices for communication with one or more physician accessible prescribing devices 4 having point of prescription applications 10. This communication between the data center server 8 and the physician accessible prescribing device may be direct or indirect. Generally, the data center server 8 will include processor control instructions for communications between physician accessible prescribing devices 4 for prescription related data exchange as will be described in more detail below. Of course, the data center server 8 may be implemented by multiple servers accessible over open and/or private or otherwise secure networks. The database of such a prescription messaging data center server may include the information of a PBM or otherwise have access to a PBM over the network 6. Furthermore, the database of the prescription messaging data center server 8 may also include alternative drug associations and messages associated with recommending such alternative drugs to physicians as will be explained in more detail herein.

In general, the physician assist system 2 may also include distribution related systems such as one or more servers associated with pharmacy systems 12. Generally, the pharmacy system 12 is accessible by the network 6. It is preferred that the pharmacy system 12 be enabled for receiving or processing prescription requests or orders for distribution of medication to a patient of the physician. Thus, in a typical arrangement, the pharmacy system 12 may electronically receive a prescription over the network 6. Since this information is preferred to be confidential, such electronic communication may be via encrypted electronic data messaging or other secured communication such as a telephone facsimile transmission received by the pharmacy system 12.

Other arrangements of the components of such a physician assist system 2 will be apparent to those skilled in the art. For example, the components may be arranged as the electronic prescription system disclosed in U.S. patent application Ser. No. 09/653,123 filed Aug. 31, 2000, the contents of which have been incorporated herein by reference.

In general, such systems will share electronic patient information and drug/medication information as discussed herein, which may be stored in various devices or databases of the system. Data sharing between such systems may be periodic as in a synchronization scheme. Such sharing may also be transferred by a communication means as needed when such information is requested at any given time by a device of the system.

As previously discussed, the physician accessible prescribing device 2 of the system when equipped for entering electronic prescriptions includes a point of prescription messaging application 10. A description of an operation controlled by the control code of such an application will now be described with respect to a preferred embodiment.

Figure 3:
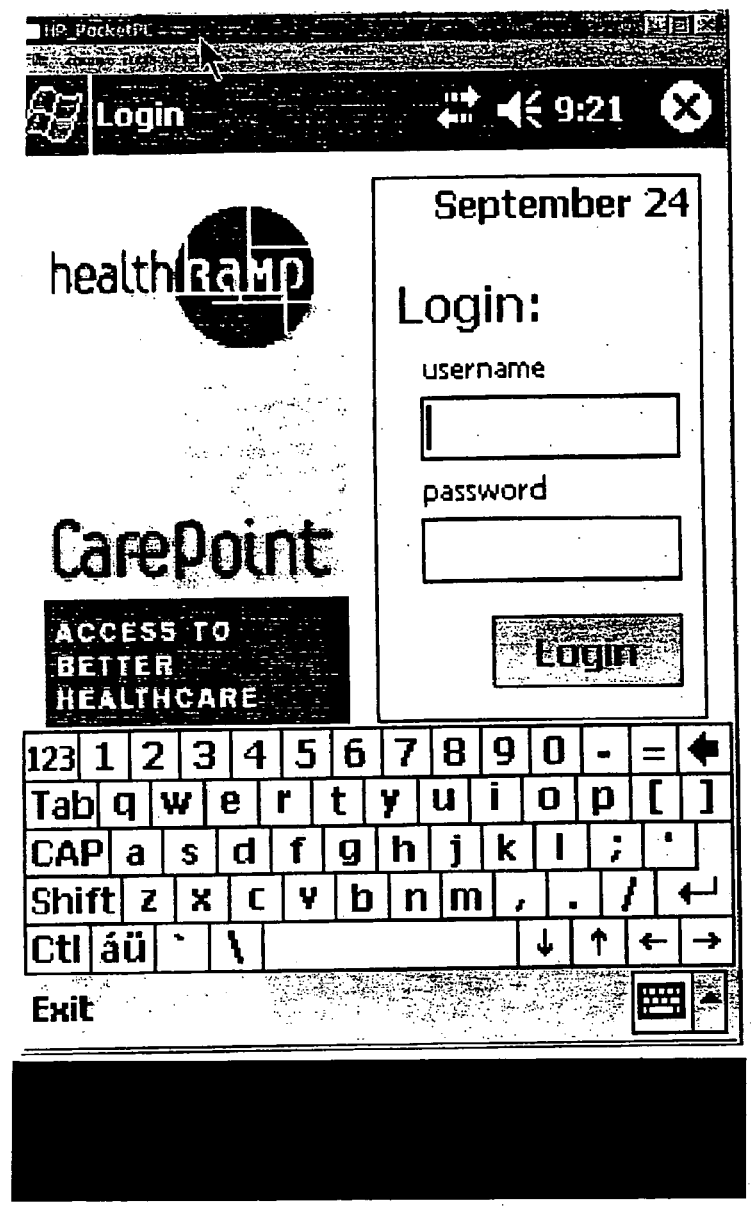
FIG. 3 is a user interface of a point of prescription application illustrating a prescriber login to a physician assist system of the invention.
Figure 4:
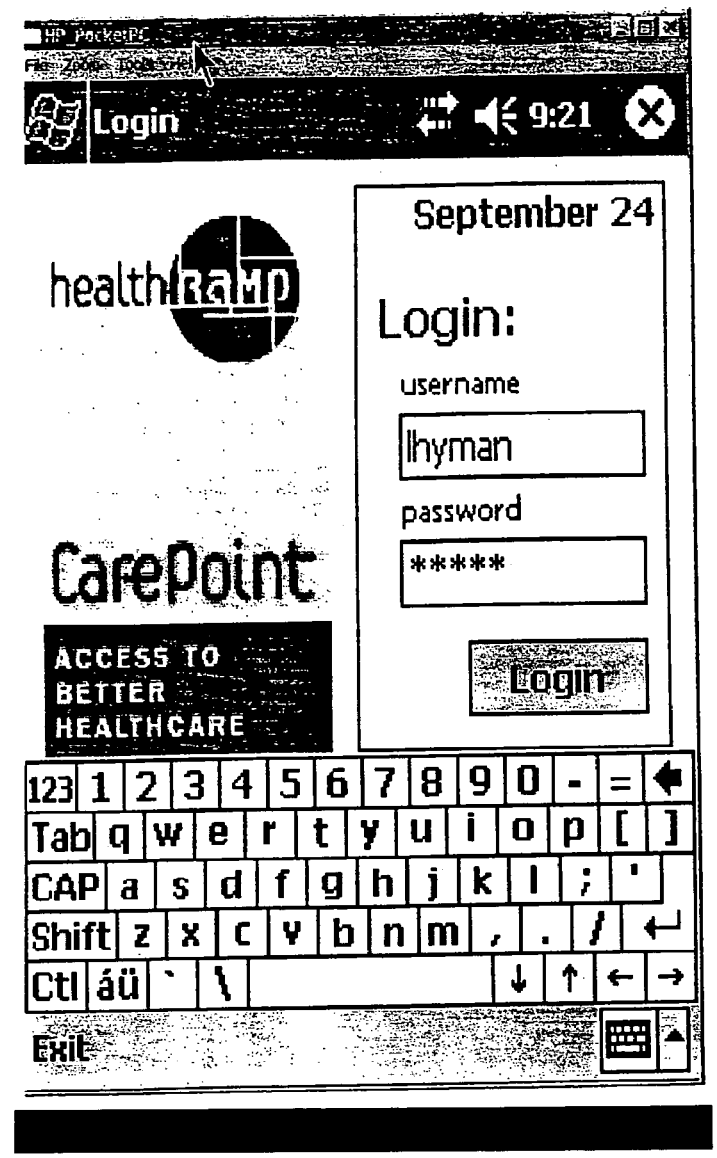
FIG. 4 is a the user interface of FIG. 3 after entry of username and password.
Figure 5:
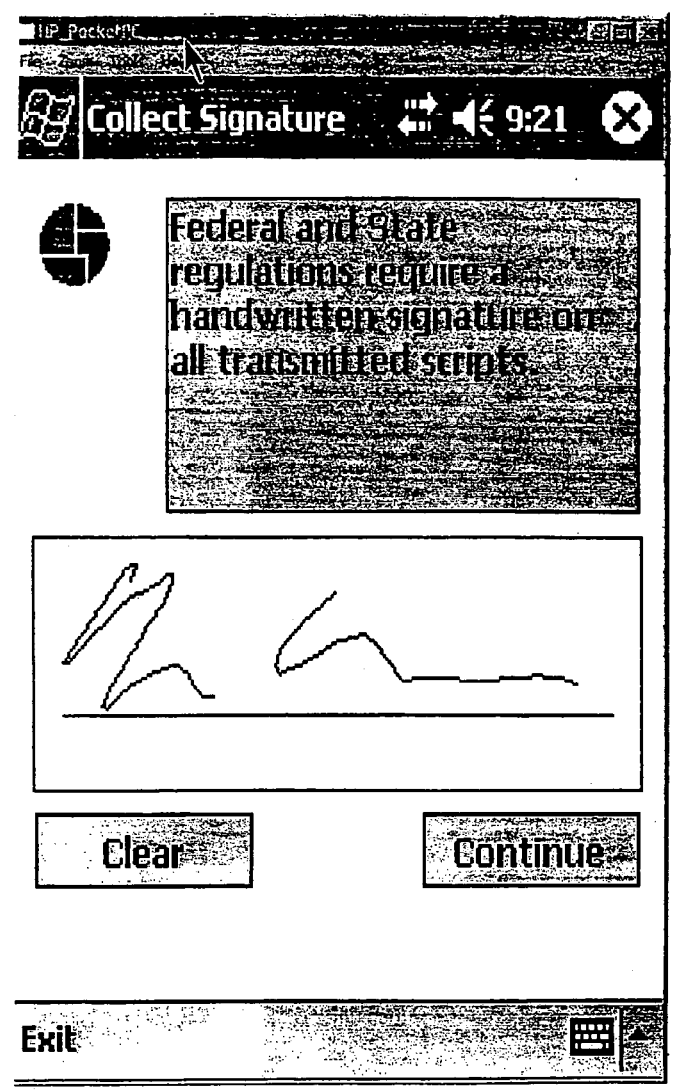
FIG. 5 is a signature input user interface of a point of prescription application corresponding to the login procedure of the physician assist system of the invention.
Figure 6:
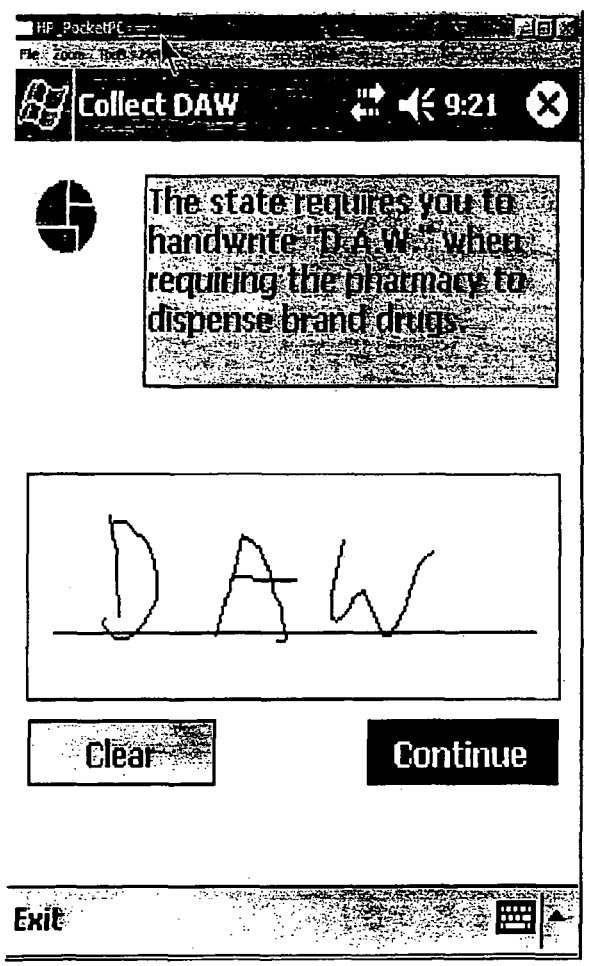
FIG. 6 is a further login screen of a point of prescription application used in authorizing electronic prescribing of drugs in the physician assist system of the invention.

In this example of operation, a physician-prescriber operates prescribing device 4 with the physician assist system for the purpose of prescription generation as illustrated with regard to the user interface illustrations of FIGS. 3 to 22. Initially, for security purposes, a login screen is displayed (FIG. 3) prompting the prescriber to enter login information. Logging in preferably includes entering login information which may include electronic signature and/or a handwriting samples (FIGS. 4-6).

Figure 7:
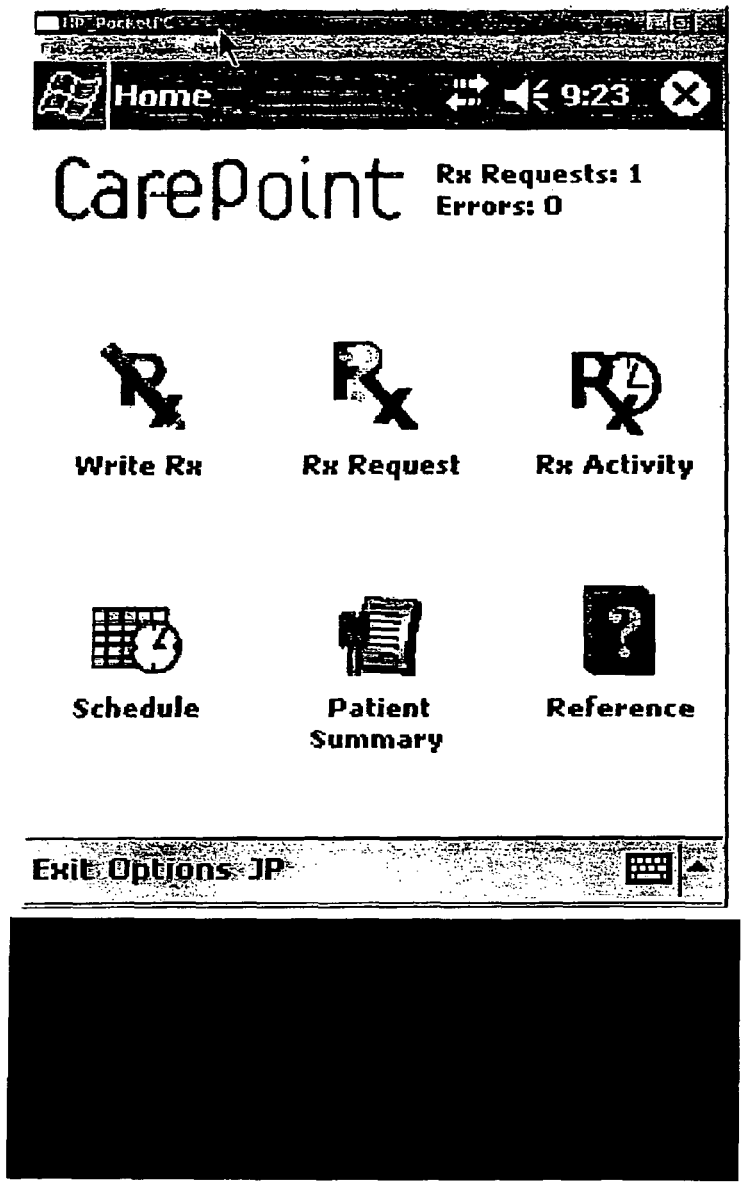
FIG. 7 is a menu user interface of a point of prescription application with icons for providing access to prescribing and alternative medication suggesting routines of the invention.
Figure 8:
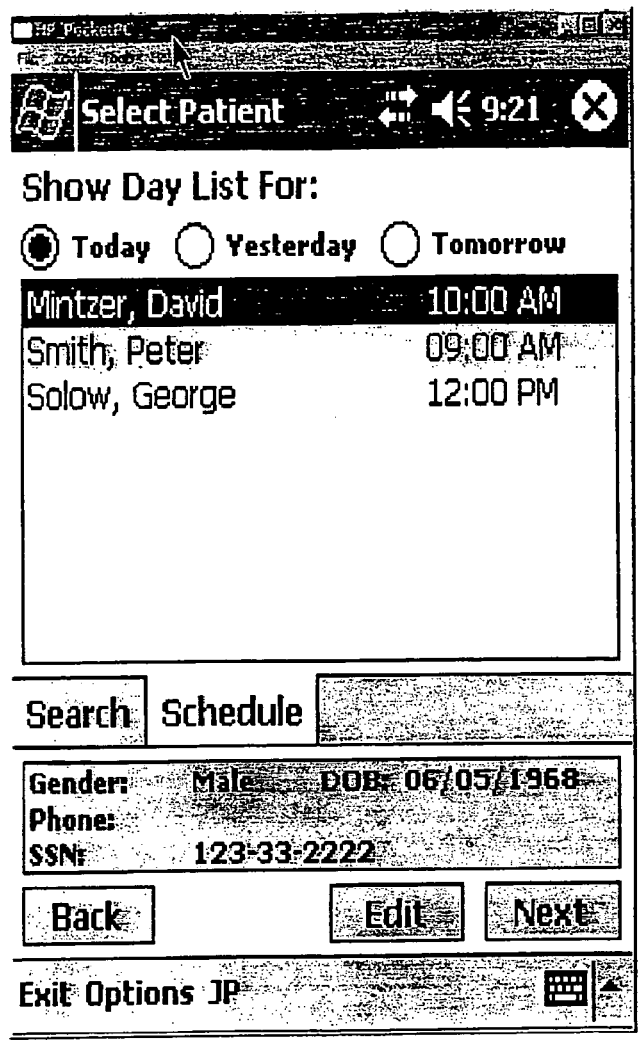
FIG. 8 is a patient list user interface of a point of prescription application for whom medications may be prescribed according to a selection of an alternative medication suggestion of the invention.
Figure 9:
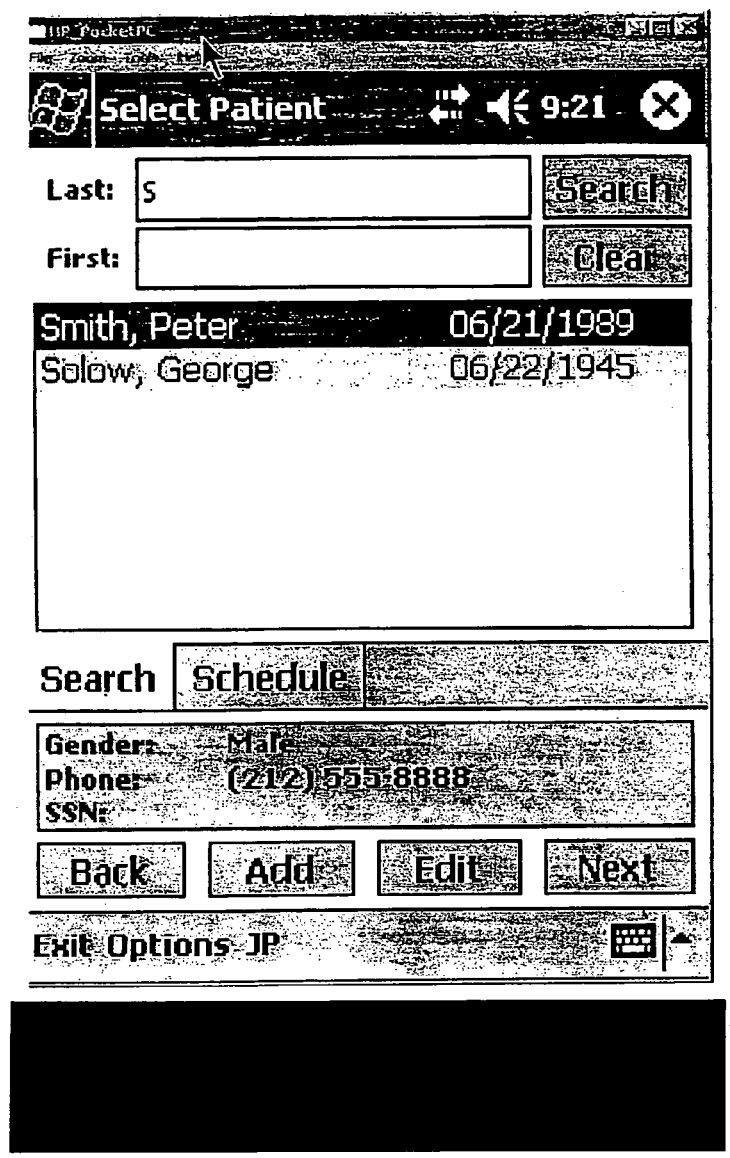
FIG. 9 is another patient list user interface of a point of prescription application for whom medications may be prescribed according to a selection of an alternative medication suggestion of the invention.
Figure 10:
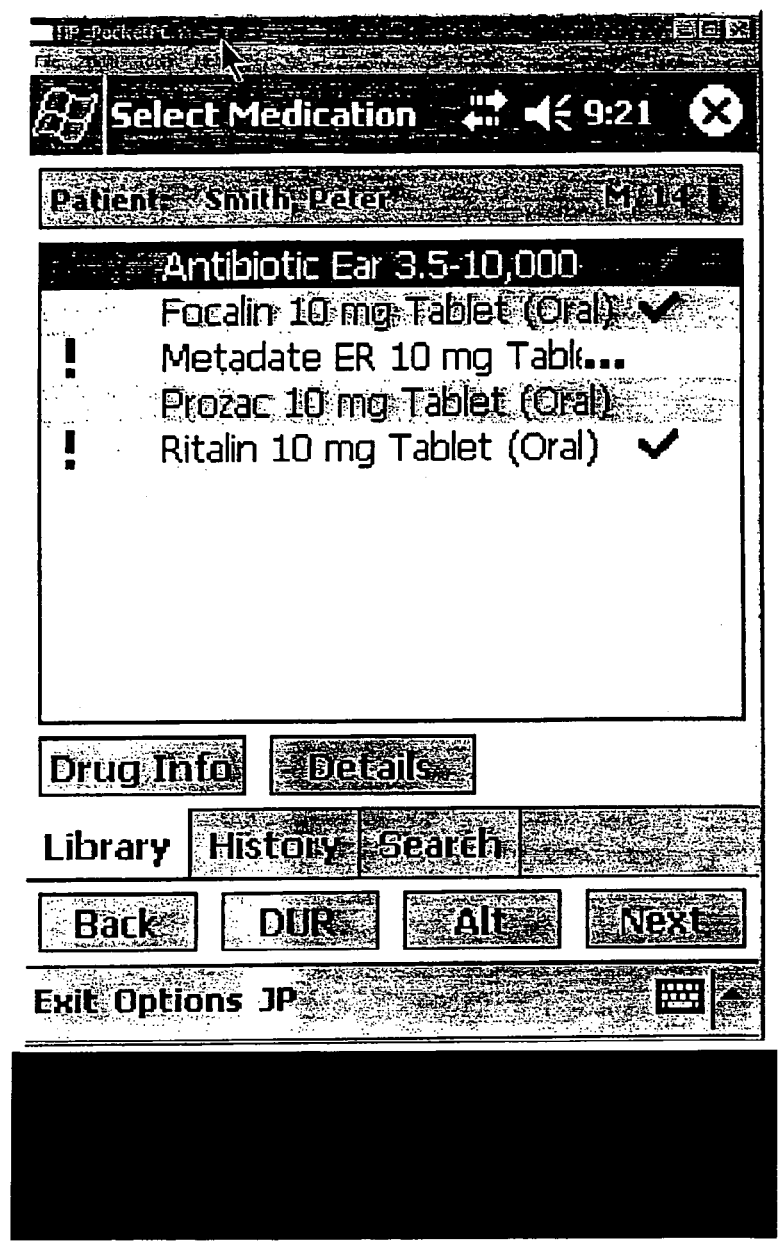
FIG. 10 is a prescription history list user interface showing various past prescriptions of a point of prescription application with action icons for performing DUR functions and accessing drug information.
Figure 11:
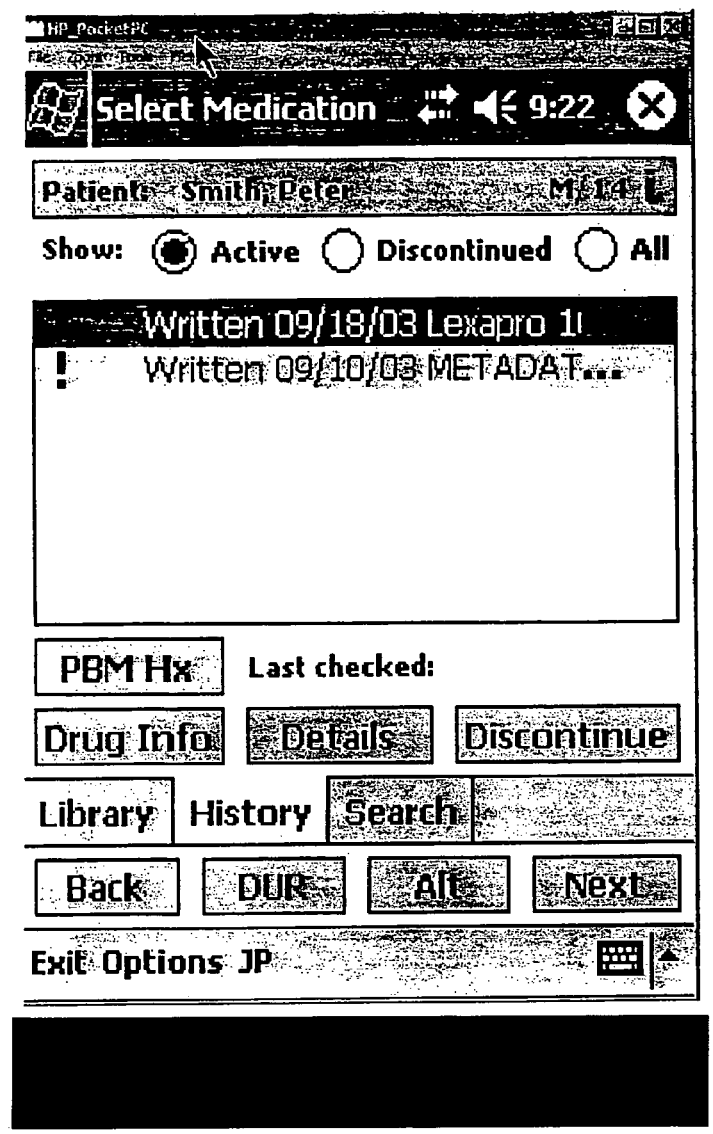
FIG. 11 is a prescription description user interface of a point of prescription application showing one prescription from the prescription history list of the user interface of FIG. 10 with action icons for performing DUR functions, accessing PBM history and requesting drug information.

The prescriber then may be prompted to select a schedule of patients by the appearance of a schedule icon (FIG. 7). With selection of the schedule icon, a patient list may be viewed for selection of a particular patient (FIG. 8 or 9). In general, access to the patient's medical history may be provided with this application on the prescribing device. Preferably, a list of medications is displayed for the patient as illustrated in FIG. 10. From such a list, the prescriber can select a medication that was prescribed to the patient, as in the example one that contains Prozac, and view related prescription information (e.g., date of prescription and prescribing doctor) (FIGS. 10 and 11). Such patient information may be accessed on the prescribing device 4, for example, as a patient and/or prescription information files. However, if not, such information may be requested from the physician database system 5, the prescription messaging data center 8, and/or the pharmacy system 12.

Figure 12:
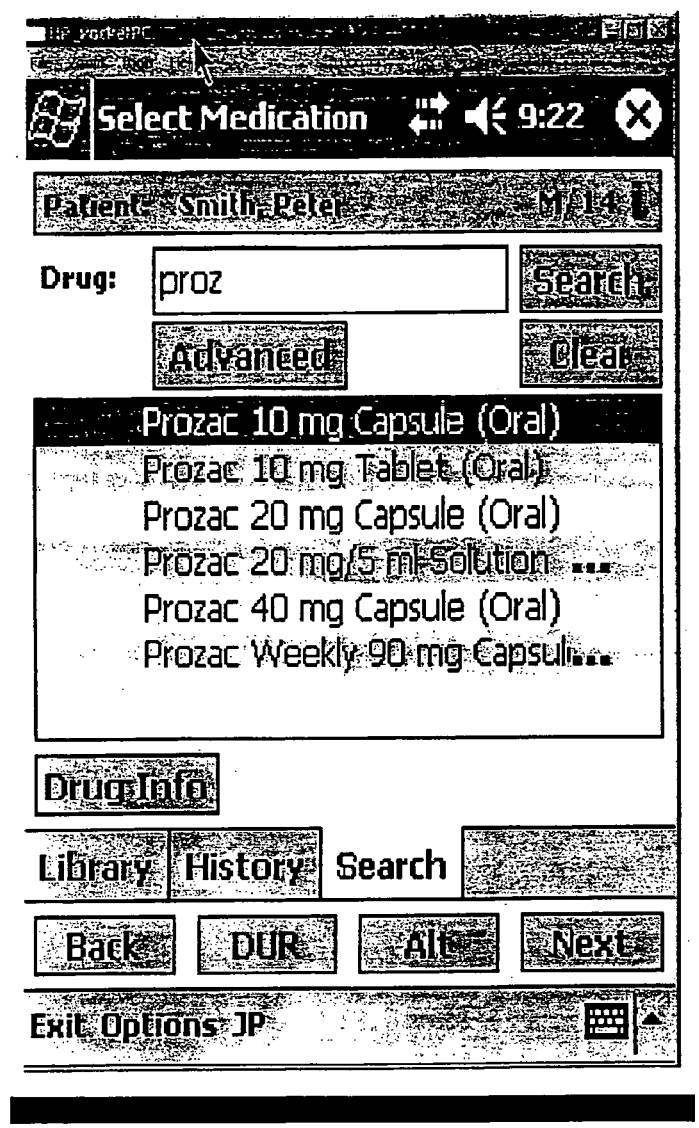
FIG. 12 is a search user interface of a point of prescription application for accessing information concerning particular brands of medications.
Figure 13:
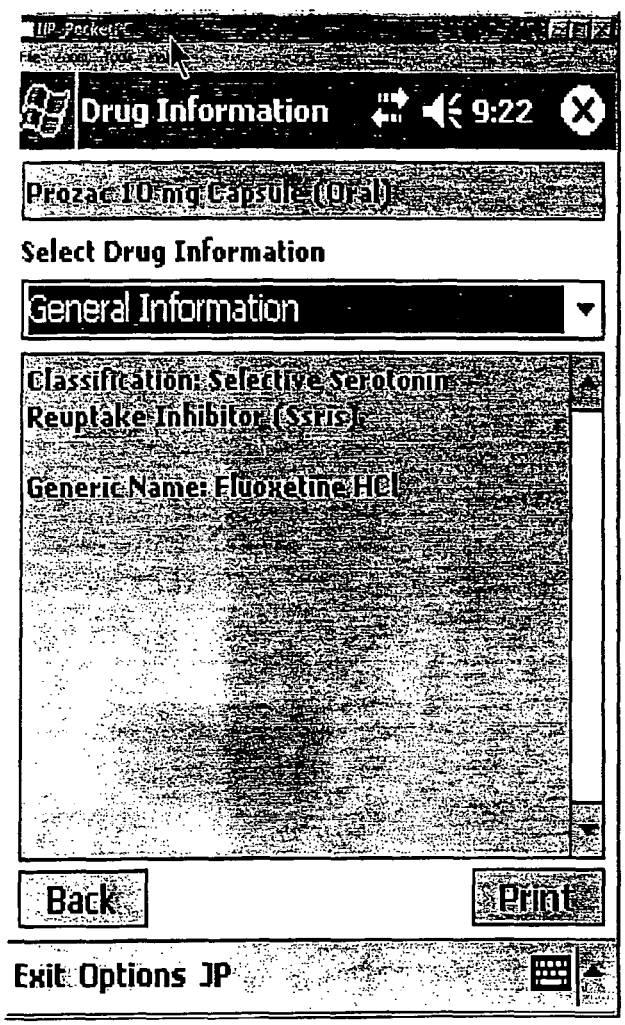
FIG. 13 is a drug information user interface of a point of prescription application for displaying information about a selected drug searched by the interface of FIG. 12.

As illustrated in FIG. 12 a list of available forms of the selected medication Prozac may be displayed. From the list, a specific medication may be selected (10 mg capsule oral). In further response to selection, drug information is displayed as illustrated in FIG. 13. Such drug information may be accessed on the prescribing device 4, for example, as a drug information files. However, if not, such information may requested from the physician database system 5, the prescription messaging data center 8, and/or the pharmacy system 12.

Figure 14:
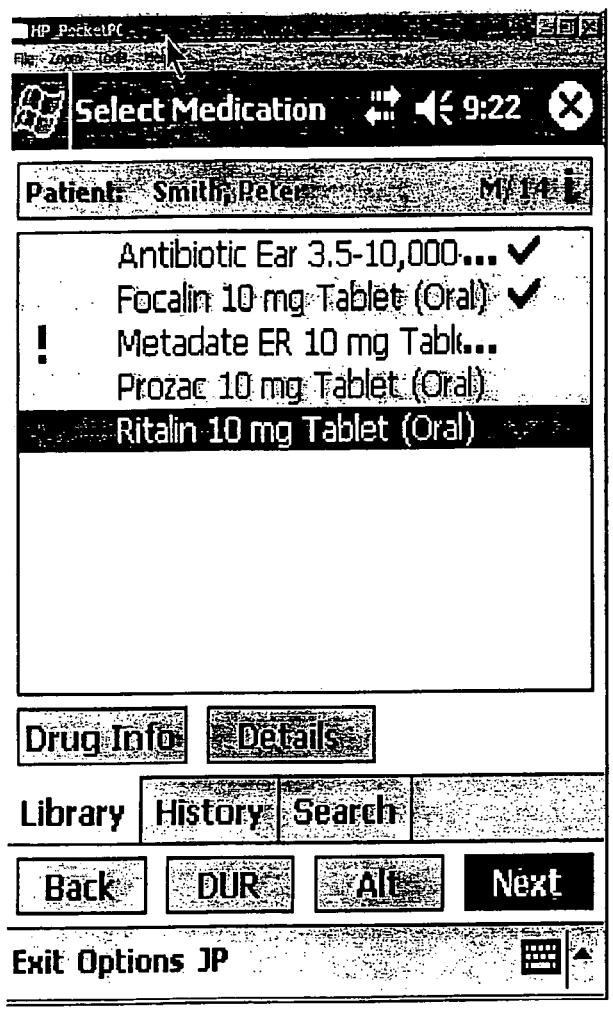
FIG. 14 is a medication selection user interface of a point of prescription application for selecting a medication to generate an electronic prescription for a patient.
Figure 15:
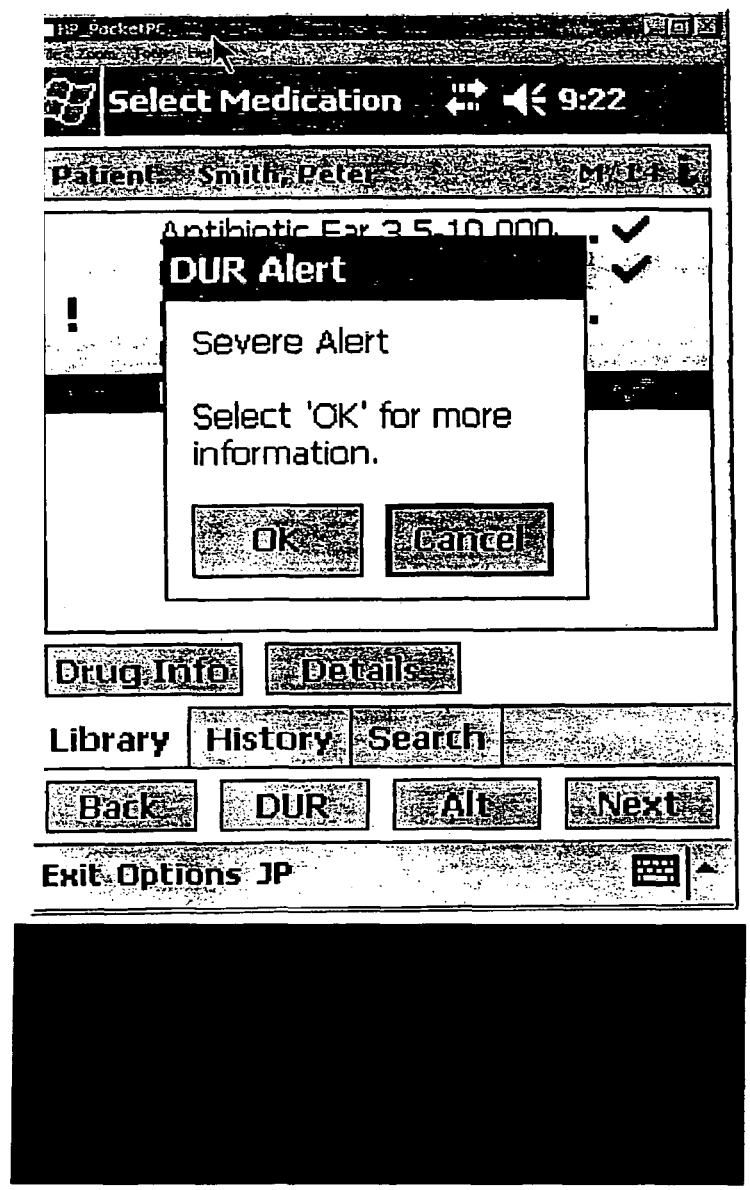
FIG. 15 illustrates an automated DUR alert from the user interface of FIG. 14 upon selection of a medication with the user interface of FIG. 14.
Figure 16:
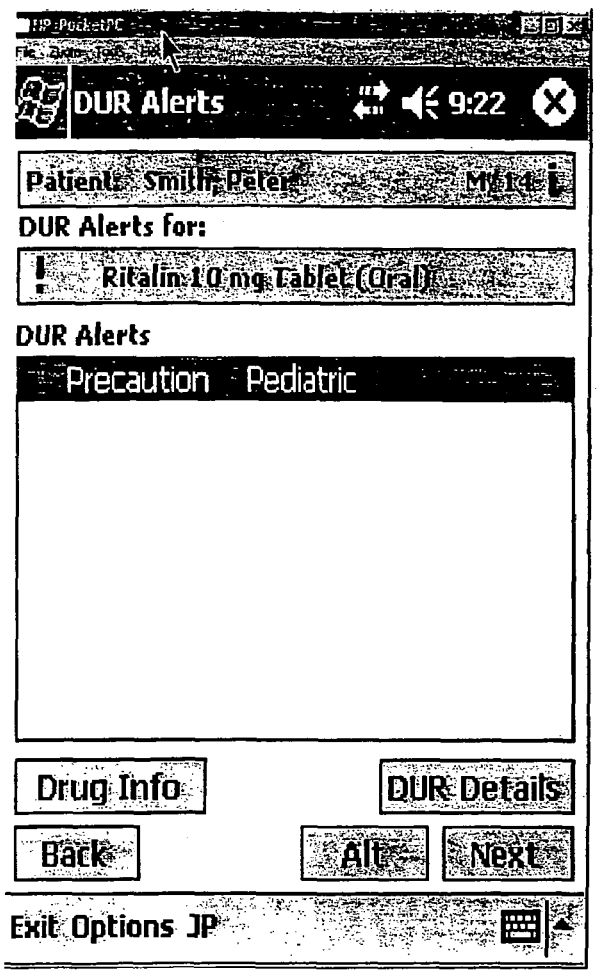
FIG. 16 illustrates presenting of further DUR information concerning the alert of FIG. 15 in the point of prescription application.
Figure 17:
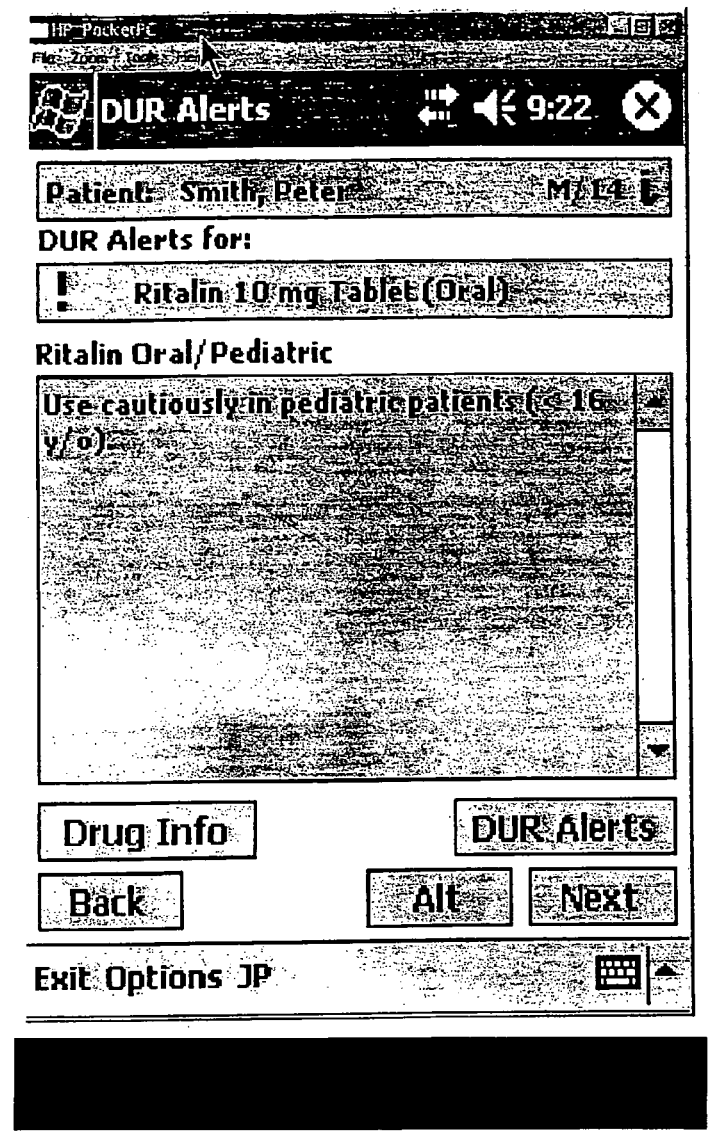
FIG. 17 illustrates presenting of still further DUR information concerning the alert of FIG. 15 in the point of prescription application.

The prescriber may also return to again view the list of medications for the patient as illustrated in FIG. 14. The prescriber then may select another medication, (e.g. Ritalin 10 mg). AS illustrated in FIG. 15, such selection may be followed by conducting a DUR ("drug utilization review") alert which is displayed if the prescriber proceeds in selecting that medication ("DUR Alert—Severe Alert"). Examples of such alerts are illustrated in FIGS. 15, 16 and 17. Of course, such an alert may be based on data currently or previously requested from a PBM over the network.

Additionally, the point of prescription messaging application 10 is configured with the control instructions for generating display of medication messages 21 suggesting one or more alternative medication(s) associated with a medication selection made on the prescribing device 4. In this regard, alternative medication suggestions 20 may be accompanied by a sponsor information message 22. Such messages may be based on data (e.g., associations between medications and alternative medications from different sponsors, and sponsor messages) stored on the prescribing device 4 or transferred from prescription messaging data center 8 as a result of a request based on the selection of the original medication or otherwise.

Figure 18:
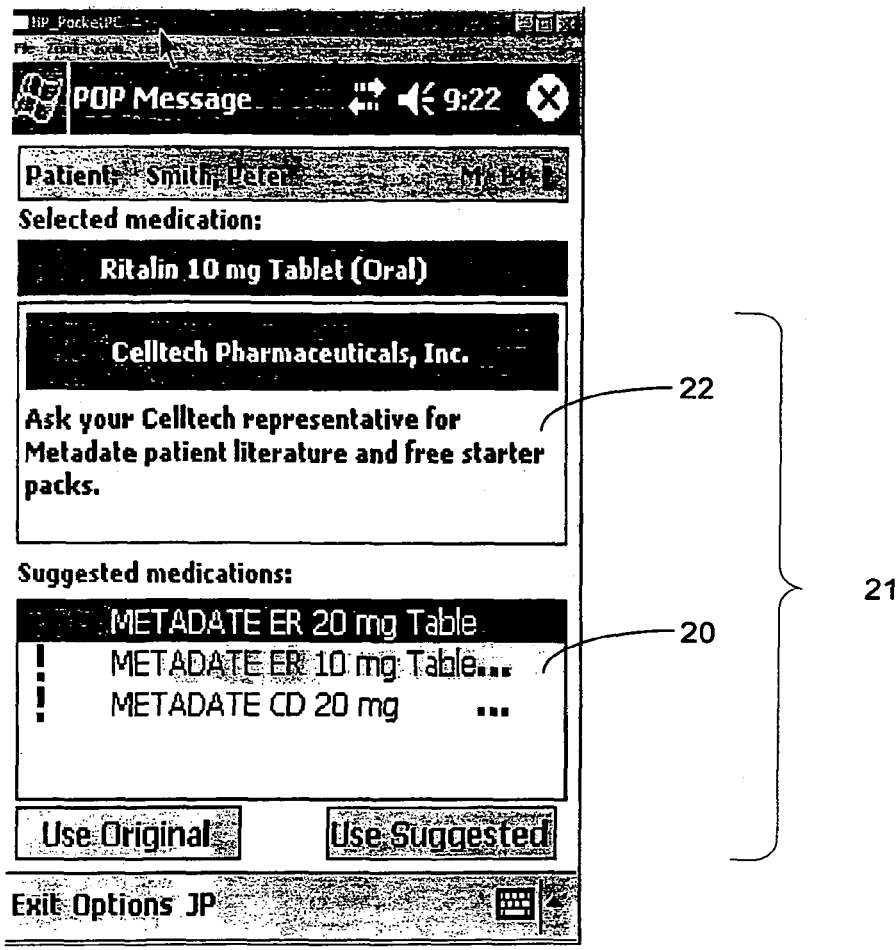
FIG. 18 illustrates a user interface of a point of prescription application with automated display of sponsor messages concerning alternative suggested medications associated with a selected medication, displayed in response to the selected medication, with action items for initiating functionality of selecting the original selected medication or a suggested alternative medication.
Figure 19:
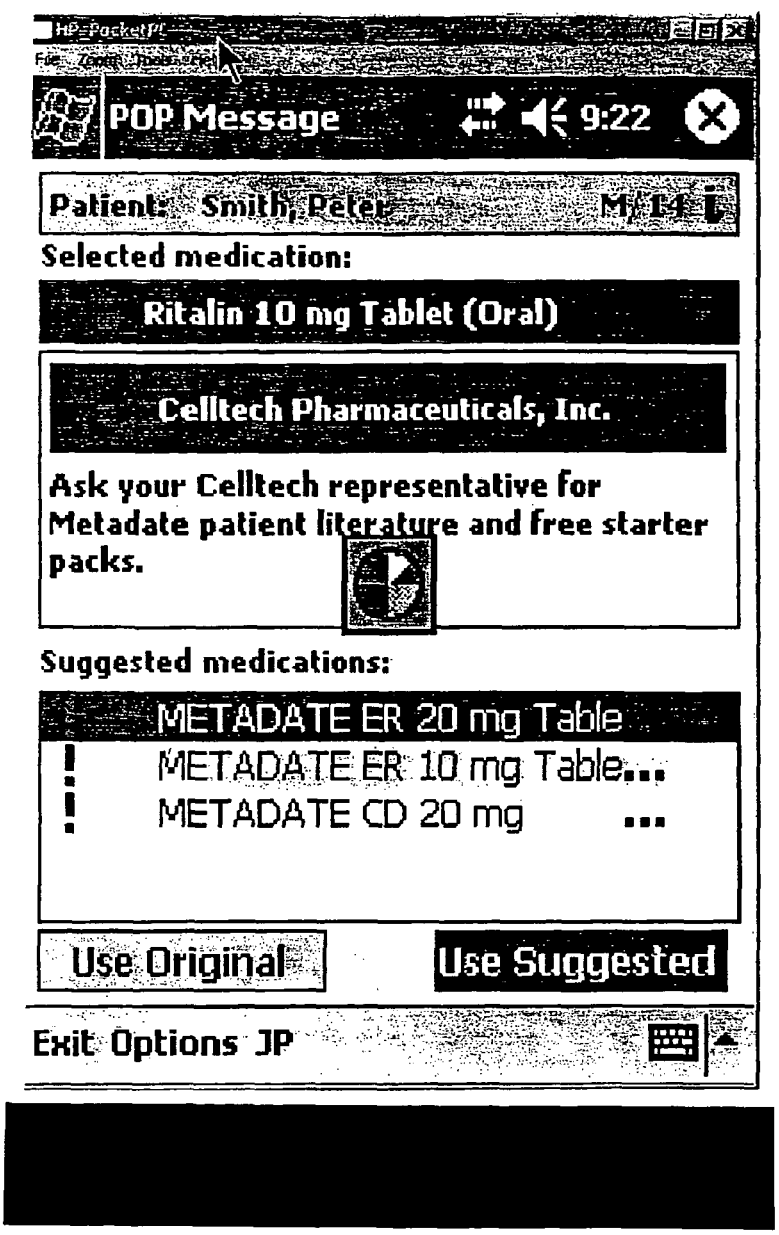
FIG. 19 illustrates selection of the action item initiating the functionality of selecting an alternative suggested medication in the user interface of a point of prescription application of FIG. 18.
Figure 20:
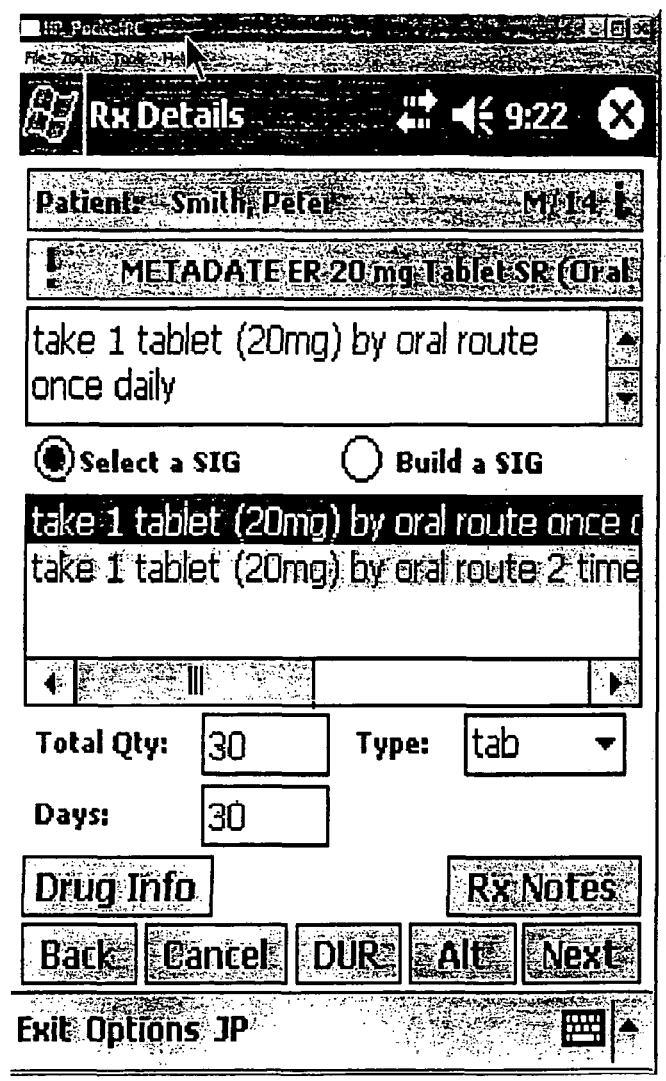
FIG. 20 illustrates a user interface of a point of prescription application showing further messages associated with the alternative suggested medication including several dose and usage instructions for the alternative suggested medication, also with action items for initiating of access to drug information for or performing a DUR with the alternative suggested medication.
Figure 21:
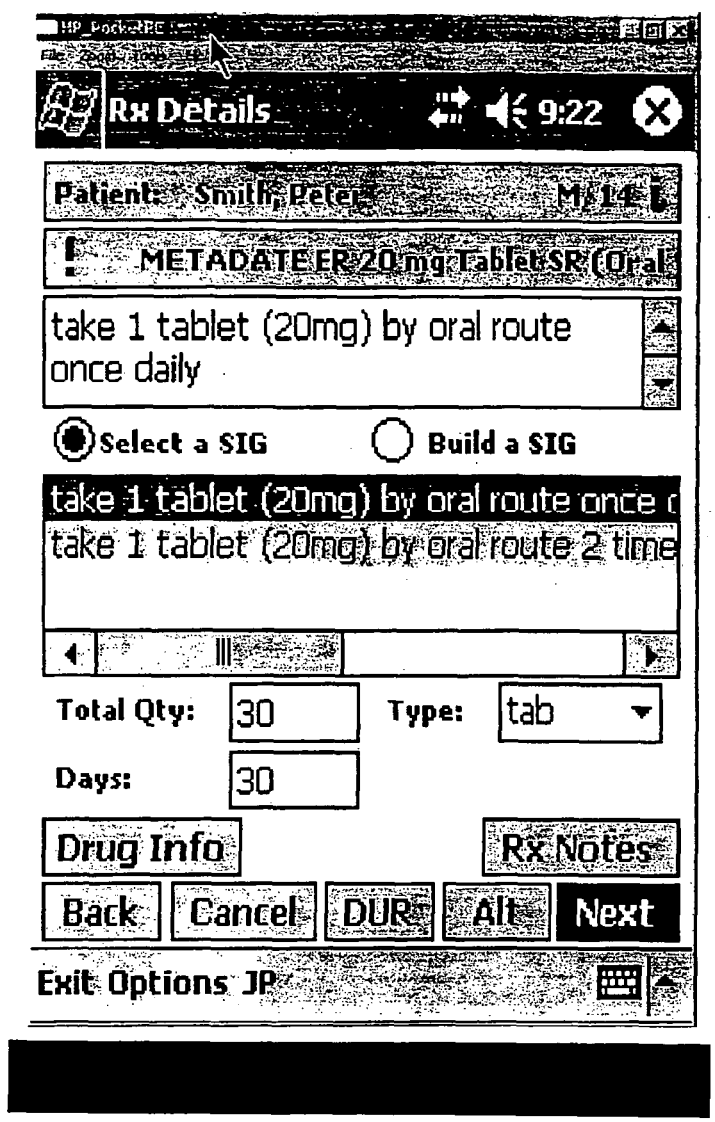
FIG. 21 is the user interface of FIG. 20, illustrates activation of a next icon for initiation functionality of completing selecting the alternative suggested medication with a default dose and usage instruction for an electronic prescription.

For example, as illustrated in FIGS. 18 and 19, if the prescriber proceeds in selecting Ritalin, point of prescribing messages are displayed if that medication has an association with alternative medications of a different sponsor. Thus, an alternative medication suggestions 20 sponsored by a maker of another medication may be displayed. The sponsor, seller or maker can define any number of such messages for one or more alternative medications. When such a message is launched, multiple messages can be cycled in the display of the prescribing device 4 according to a predetermined sequence such that a detailed presentation may be provided about the alternative medication.

In the illustrated example, the messages are generated in response to Ritalin selection. In response, a different medication (Metadate) is suggested for treating the same condition in a suggested medication list. Moreover, an alternative medication message 22 suggesting the prescription of an alternative medication is displayed based on the prescriber selecting the particular medication. This message illustrates providing information to the prescriber on contacting the source of the alternative medication (e.g., the sponsor, seller or maker of the alternative medication), for example, to find out information about the medication. The message may also suggest one or more "SIG"(s) (i.e., doses and/or usage instructions related to prescribing the alternative suggested medication (e.g., "take one tablet (20 mg) by oral route once a day before bedtime"). Such dose and usage instruction messages are illustrated in the user interface of FIG. 20. The prescriber may select a suggested dose and usage instruction, use a default suggested dose and usage instruction or create a custom one that can then be incorporated into a prescription.

Stated another way, the originally selected medication provides a 'trigger' for displaying a message suggesting an alternative 'target' medication. While alternative medications or messages of a sponsor common to the trigger medication may be displayed, the display of messages suggesting the alternative medication is typically based on the suggested medications of a different sponsor or maker. Such messages offer a way for sponsored promotion of other brand name medications to the prescriber as an alternative to the selected brand name or generic medication at the point of prescription.

Typically, an electronically stored table or other database type data structure is used to relate or associate the trigger medications to target medications. Preferably, information about each medication is stored and displayed by a drug name, a strength, a dose form, and a route of administration; e.g., Ritalin 10 mg Tablet (Oral)). Of course, complete medical information concerning the drug may also be accessed or view with the prescribing device 4. When the prescriber selects a medication on the prescribing device, the table is consulted electronically in response thereto either locally or via communications such as over the network 6. If the medication is a trigger medication, a message suggesting the target medication is then displayed.

One such table is shown for purposes of illustration in FIG. 23. Those skilled in the art will recognize other data structures and programming techniques for implementing a display of messages based on alternative medication suggestions as discussed herein. In the illustrated table, selected Medication-A offered or made by Sponsor-A has six possible alternatives associated with it. These include Medication-B, Medication-BB, Medication-BBB, each from Sponsor B. Alternative medications labeled Medication-C and Medication-CC are sponsored by different Sponsor-C and are also associated as alternatives of Medication-A. Finally, alternative Medication-AA of Sponsor A is also an alternative of Medication-A. Such alternatives and their associations as represented by the table structure would be previously determined based on the medical information associated with the medications if such medications are equivalently used for a particular patient diagnosis such that either one may be selected. However, such associations need not strictly be intended for alternative use but may indicate use in conjunction with the originally selected medication to the extent that they relate to a common patient diagnosis. Optionally, the associations may simply be based on associations specified by a particular sponsor, maker or seller of such targeted medications without relation as an alternative drug equivalence or any relationship to a given diagnosis for a patient.

In a preferred embodiment, the table optionally includes additional data condition(s) (one or more) that help to determine whether any alternatives will be displayed in response to the medication selection and the content of such message. Thus, in response to the selection, the table is checked to determine if one or more alternative medications should be displayed based on the association between the trigger and target medications as well as any additional preset condition(s). For example, the table may include conditions based on the age and/or gender of the patient. In such a case, when the trigger medication is selected by the prescriber, the particular target medication displayed can differ based on the patient's age and/or gender.

An example of such a table is illustrated in FIG. 24 with sample conditions based on age and gender. Thus, for a female patient based on the existing hypothetical table example, if a Medication-A is selected, Medication-C would not be suggested. If the female patient was over 18 years of age, Medication-BB would also not be suggested. Thus, for this patient, of the six associated medications, only the remaining four would be displayed (i.e., Medication-B, Medication-BBB, Medication-CC, and Medication-AA).

Other embodiments of the system may include other conditions or factors controlling the display of alternative suggested medications (targets). For example, display of a particular message or suggestion of a particular target medication can be conditioned on the location of the prescriber or patient, e.g., location within a particular region of the United States such as Northeast, Southeast, Midwest, state, county, town, etc. Thus, for the above example, if the female, over 18 patient was in a Northern region, upon selection of Medication-A, Medication-C and Medication-CC would be excluded. Thus, only Medication-B and Medication-BBB would be displayed as suggested alternatives.

Finally, a date condition may also be applied, for example, based on when an insurance plan, sponsor or maker intends to phase out or phase in a medication. Similarly, such a date filter may simply relate to a particular period of time that a sponsor desires to have its medications suggested as alternatives. Thus, with regard to additionally applying a date filter or condition to the above example, if the selection by the prescriber was being made for after Jan. 1, 2001, Medication-BBB would be excluded and only Medication-B would be suggested as the target for the prescriber's selection of Medication-A.

In this way, the display of alternative suggested medications may be filtered by various conditions to save the physician time from selecting a suggested medication for the patient that would not be appropriate and would have to be subsequently changed after it is discovered that it was an inappropriate selection for any given reason. The system may also be implemented to maximize the presenting of education information pursuant to a desired set of conditions specified or desired by a sponsor. While the illustrated filtering conditions of FIG. 24 include age, gender, region and date, other conditions for filtering suggested medications, for example, such as a sponsor or maker condition, may be implemented. Thus, the application may control restricting any sponsor from designating a trigger medication for more than one group of target medications or only the display of a single sponsor's alternative medication suggestions may be implemented. Similarly, the same medication may be controlled such that it cannot be a trigger for more than one sponsor in any designated region.

Optionally, additional control conditions or rules for displaying associated alternative medications may include a set maximum number of times to show messages to a particular physician for a group of target medications. The application may also control how frequently to trigger a message. For example, the message for any given alternative may be shown every time a trigger medication is selected, every other time, every third time, etc. Preferably, a message will not be triggered more than once for a single prescription.

Furthermore, such conditions in determining whether the display of a target or alternative medication in response to selection of a trigger medication may additionally be based on other patient information such as first, second, third, etc. diagnoses data of the patient such as if the target medication would be inappropriate or appropriate for one or more of such diagnoses which may or may not be common with a diagnosis for which the trigger medication was selected. In this event, medication or drug related data with regard to the particular diagnoses for which the suggested medication is prescribable would be compared to the patient's actual diagnoses.

Subsequently, with the presented alternative suggested medication, filtered by these conditions or otherwise, the prescriber may choose to prescribe a presented target medication. This selected medication, as with the original trigger medication, may also be automatically subjected to an electronic DUR for checking for conflicts with the patient's history or the patient's insurance plan on the prescribing device 4 and informing the physician of the results. In this event, patient name, social security data, address or other patient identifier information may be used when checking the medication. However, the DUR and formulary requirements may also alternatively be implemented as conditions restricting the display of an alternative medication suggestion or target medication if it would not satisfy the DUR or formulary restrictions of the patient and plan, thus, preventing the prescriber from reviewing the suggested medication if it did not satisfy the DUR and formulary requirements. This may be achieved by automated remote access to PBM information over the network 6 or by automated access to previously stored information on the prescribing device 4.

Figure 22:
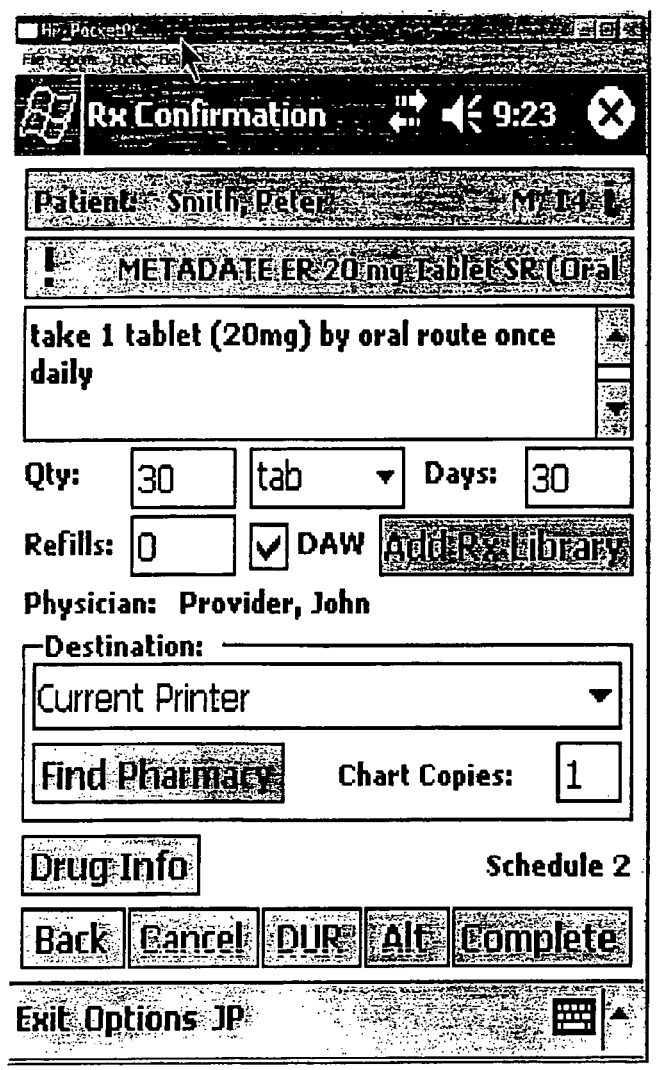
FIG. 22 is a user interface of a point of prescription application in response to the selection from the user interface of FIG. 21, displaying action items for finalizing an electronic prescription.

Of course, the prescriber may disregard the alternatives suggested and prescribe the original selected trigger drug. The prescriber may even delete or cancel the selected original drug, select a presented alternative target medication which is not equivalent to the original as well as selecting another alternative target medication which is equivalent to the original selected medication. As illustrated in the example shown in FIGS. 19, 20 and 21, upon selecting the alternative suggested medication and the prescriber may proceed to generate an electronic prescription. As illustrated in FIG. 22, the prescription process may be completed by using the application to initiate a transfer of the created electronic prescription to a pharmacy system 12 over the network 6.

Thus, the resulting prescriptions are automatically sent to a patient's pharmacy with a simple click of a button via secure communication such as via a fax telephone line. Prescriptions can also be printed for chart copies or for patients. Because the prescriber's signature is captured at the session login, it can appear on all prescription scripts written during that session.

Optionally, the point of prescription messaging application 10 may also control tracking of information associated with targeted medication suggestions. For example, for each physician in a practice or based on a group of physicians of a practice, the application can record the number of times a message was triggered for any targeted medications. For prescribed targeted medications, it may also record whether or not the target medication was chosen as a result or in connection with the display of a triggered message, and, if so, which message was displayed. This tracking of data may also include monitoring of which medication was originally chosen, as well as the DUR and formulary status of both the original triggered medication and the target medication for purposes of future comparison.

Sponsors can benefit from providing targeted messages that offer alternative drugs at the point of prescribing. Physicians and patients benefit when the prescriber or physician selects a designated trigger medication because a sponsor-defined point-of-prescribing message is displayed that will identifying the sponsor and educate the physician on one or more beneficial alternatives to the medication selected.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method comprising:
   prompting, via a user interface of a device, a prescriber to enter an electronic handwriting sample during a login process;
   synchronizing, via an encrypted communication interface, the device with information pertaining to a first medication;
   receiving, at the device and via a first user interface of a messaging application executing on the device, a selection of a first medication from a database;
   synchronizing, via the encrypted communication interface, the device with information from a prescription messaging data center server implemented by multiple servers accessible over secure networks and equipped with one or more communications devices for communication with one or more prescribing devices having point of prescription applications, and including processor control instructions for communications between the prescribing devices for prescription related data exchange, and including a database of one or more other medications and messages associated with recommending such one or more other medications;
   determining, by a processor and based on one or more associations between the first medication and the one or more other medications, at least one of the one or more other medications that are alternative medications to the first medication;
   identifying, by the processor and among the at least one of the one or more other medications that are determined to be alternative medications to the first medication, one or more restricted medications;
   excluding, by the processor, the one or more restricted medications from the at least one of the one or more other medications that are determined to be alternative medications to the first medication;
   providing, via a second user interface of the messaging application executing on the device and in relation to the first medication, information of one or more remaining medications from the at least one of the one or more other medications that are determined to be alternative medications to the first medication;
   generating an electronic prescription pertaining to the one or more remaining medications; and
   initiating an automatic transfer of the generated electronic prescription to a pharmacy system via a secure communication interface.

2. The method of claim 1 wherein the one or more remaining medications from the at least one of the one or more other medications that are determined to be alternative medications to the first medication comprises a sponsored medication.

3. The method of claim 1, wherein the restricted medications comprise medications that are restricted with respect to at least one of (a) a gender of a patient, (b) an age of a patient, or (c) a geographic region of at least one of a prescriber or a patient.

4. The method of claim 1 wherein the one or more associations between the first medication identifier and one or more identifiers corresponding to one or more other medications relates the associated medications by equivalence.

5. A method comprising:
   prompting, via a user interface of a device, a prescriber to enter an electronic handwriting sample during a login process;
   synchronizing, via an encrypted communication interface, the device with information from a database pertaining to one or more trigger medications;
   receiving, at the device, via a first user interface of a messaging application executing on the device and with respect to a patient, a selection of at least one of one or more trigger medications, the selection being associated with at least one of (a) a geographic region, (b) a date, (c) an age, or (d) a diagnosis;
   synchronizing, via the encrypted communication interface, the device with information from a data center server implemented by multiple servers accessible over secure networks and equipped with one or more communications devices for communication with one or more prescribing devices having point of prescription applications, and including processor control instructions for communications between the prescribing devices for prescription related data exchange, and including a database of one or more target medications and messages associated with recommending such one or more other medications;
   comparing, by the processor, the at least one of (a) the geographic region, (b) the date, (c) the age, or (d) the diagnosis that are associated with the selection of the at least one of the one or more trigger medications with at least one of (a) a geographic region, (b) a date, (c) an age or (d) a diagnosis that are associated with at least one of the one or more target medications that are associated with the one or more trigger medications;
   based on a determination that at least one of (a) the geographic region, (b) the date, (c) the age, or (d) the diagnosis that are associated with the selection of the at least one of the one or more trigger medications that corresponds to the target medication are respectively comparable to (a) the geographic region, (b) the date, (c) the age, or (d) the diagnosis that are associated with the at least one of the one or more target medications that are associated with the one or more trigger medications, providing, via a second user interface of the messaging application executing on the device, content pertaining to the target medication in response to the selection of the trigger medication;
   generating an electronic prescription pertaining at least one of the one or more target medications or the one or more trigger medications; and
   initiating an automatic transfer of the generated electronic prescription to a pharmacy system via a secure communication interface.

6. The method of claim 5 wherein the content pertaining to the target medication comprises an entity related to the target medication.

7. The method of claim 5 wherein the geographic region associated with the selection comprises information pertaining to at least one of a location of prescribing or a location of the patient.

8. The method of claim 5 wherein the target medication is associated with a sponsor.

9. The method of claim 5 wherein providing content pertaining to the target medication comprises a use instruction.

10. The method of claim 5 wherein the target medication is an alternative medication to the trigger medication.

11. A system comprising:
one or more processors to interact with a computer readable medium and to:
prompt, via a user interface of a device, a prescriber to enter an electronic handwriting sample during a login process;
synchronize, via an encrypted communication interface, the device with information from a database pertaining to one or more medications;
receive, via a first user interface of a messaging application executing on the device, a selection of at least one of one or more medications from a database;
synchronize, via the encrypted communication interface, the device with information from a data center server implemented by multiple servers accessible over secure networks and equipped with one or more communications devices for communication with one or more prescribing devices having point of prescription applications, and including processor control instructions for communications between the prescribing devices for prescription related data exchange, and including a database of a plurality of alternative medications;
identify at least one of the plurality of alternative medications based on one or more associations between (a) the at least one of the one or more medications and (b) the at least one of the plurality of alternative medications;
compare data pertaining to one or more criteria associated with at the at least one of the plurality of alternative medications with one or more criteria associated with the at least one the one or more medications to determine which of the at least one of the plurality of alternative medications have comparable criteria to the at least one of the one or more medications;
based on a determination that a medication from the plurality of alternative medications has comparable criteria to the at least one of the one or more medications, provide, via a second user interface of the messaging application executing on the device, content related to the medication in response to the selection of the at least one of the one or more medications;
generate an electronic prescription pertaining at least one of the one or more medications or the one or more alternative medications; and
initiate an automatic transfer of the generated electronic prescription to a pharmacy system via a secure communication interface.

12. The system of claim 11 wherein to provide content is to provide sponsored content.

13. The system of claim 11 wherein the one or more processors are further to generate a prescription for at least one of the medication or the at least one of the one or more medications.

14. The system of claim 11 wherein the one or more processors are further to provide an instruction associated with the medication.

15. The system of claim 11 wherein the one or more criteria comprise at least one of: a region, a date, a gender, or an age.

16. The system of claim 15 wherein the region comprises at least one of a presence or an absence of a drug prescription system within a particular region.

17. The system of claim 12 wherein the content identifies a sponsor.

18. The system of claim 11 wherein to provide content related to the medication is to generate a dispense-as-written prescription for the medication.

19. A computer-readable medium having instructions stored thereon that, when executed by a processor, cause the processor to perform operations comprising:
prompting, via a user interface of a device, a prescriber to enter an electronic handwriting sample during a login process;
synchronizing, via an encrypted communication interface, the device with information from a database pertaining to one or more trigger medications;
receiving, via a first user interface of a messaging application executing on the device, a selection of at least one of the one or more trigger medications, the selection being associated with a date;
synchronizing, via the encrypted communication interface, the device with information from a data center server implemented by multiple servers accessible over secure networks and equipped with one or more communications devices for communication with one or more prescribing devices having point of prescription applications, and including processor control instructions for communications between the prescribing devices for prescription related data exchange, and including a database of one or more target medications;
identifying among the one or more target medications that are associated with the at least one of the one or more trigger medications, one or more medications that are restricted with respect to the date;
excluding the one or more medications from consideration among the one or more target medications that are associated with the at least one of the one or more trigger medications;
providing, in relation to the selection of the at least one of the one or more trigger medications and via a second user interface of the messaging application executing on the device, information of one or more remaining target medications that are associated with the at least one of the one or more trigger medications;
generating an electronic prescription pertaining at least one of the one or more target medications or the one or more trigger medications; and
initiating an automatic transfer of the generated electronic prescription to a pharmacy system via a secure communication interface.

20. The computer-readable medium of claim 19, further comprising providing a name of a sponsor in relation to the one or more remaining target medications.

21. The computer-readable medium of claim 20 wherein the information of one or more remaining target medications is provided based on diagnostic information associated with the selection.

* * * * *